United States Patent [19]

Adam

[11] 4,064,140
[45] Dec. 20, 1977

[54] PROCESS FOR THE PRODUCTION OF IMINOPYRROLINONES

[75] Inventor: Jean-Marie Adam, Saint-Louis, France

[73] Assignee: Ciba-Geigy Corporation, Ardsley, N.Y.

[21] Appl. No.: 677,994

[22] Filed: Apr. 19, 1976

[30] Foreign Application Priority Data

Apr. 22, 1975 Switzerland .......................... 5143/75

[51] Int. Cl.$^2$ ..................... A01N 21/00; A61K 31/40; C07D 207/44
[52] U.S. Cl. ................. 260/326.5 FL; 260/326.5 FN; 260/326.5 L; 424/274
[58] Field of Search .............................. 260/326.5 FL

[56] References Cited

U.S. PATENT DOCUMENTS

| 3,637,746 | 1/1972 | Wei et al. ................... 260/326.5 FL |
| 3,968,122 | 7/1976 | Nazareth et al. ........... 260/326.5 FL |

FOREIGN PATENT DOCUMENTS

| 1,445,792 | 1/1969 | Germany ................... 260/326.5 FL |

*Primary Examiner*—Alton D. Rollins
*Attorney, Agent, or Firm*—Frederick H. Rabin

[57] ABSTRACT

Process for the production of iminopyrrolinones of the formula I

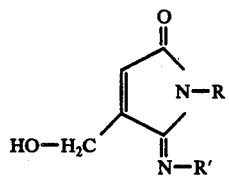

(I)

wherein one of the two substituents R and R' represents a phenyl ring unsubstituted, or substituted by $C_1$-$C_4$-alkyl, $C_1$-$C_4$-alkoxy, $C_1$-$C_4$-hydroxyalkyl, $C_1$-$C_4$-alkylamino, ($C_1$-$C_4$-alkyl)$_2$amino, halogen, nitro or cyano, whilst the other of the two substituents R and R'represents hydrogen, which process comprises reacting a chloroacetoacetanilide of the formula II $$Cl-CH_2-CO-CH_2-CO-NH-R \qquad (II)$$

wherein R has the meaning given above, in the presence of cyanide ions, in an inert solvent in the temperature range of 0° to 80° C.

15 Claims, No Drawings

PROCESS FOR THE PRODUCTION OF IMINOPYRROLINONES

The present invention relates to a chemically unique process for producing novel iminopyrrolinones of the formula I

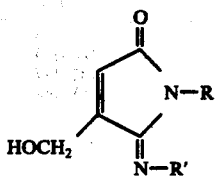
(I)

wherein one of the two substituents R and R' represents a phenyl ring unsubstituted, or substituted by $C_1$-$C_4$-alkyl, $C_1$-$C_4$-alkoxy, $C_1$-$C_4$-hydroxyalkyl, $C_1$-$C_4$-alkylamino, ($C_1$-$C_4$-alkyl)$_2$amino, halogen, nitro or cyano, whilst the other of the two substituents R and R' represents hydrogen; as well as to the novel compounds of the formula I.

These iminopyrrolinones are produced according to the invention by reacting the corresponding chloroacetoacetanilide of the formula II

(II)

wherein R represents the phenyl ring defined under formula I, in the presence of cyanide ions, preferably in the presence of alkali cyanide such as NaCN, in a solvent, to obtain by ring closure, depending on the reaction conditions, one of the two products of the formulae

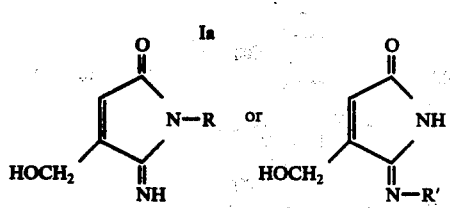

As can be seen from the reaction sequence, the substituent R' is identical to the substituent R of the formula II. The different symbols R and R' merely take into account the different positions of the phenyl substituents in the formula I.

The new process is performed in a temperature range of between 0° and 80° C, preferably however between 0° and 30° C. Depending on the choice of solvent, the process can be carried out in such a manner that there are formed almost exclusively products of the formula Ia or the bathochrome-coloured products of the formula Ib. It is also possible to use solvent mixtures, and for ring closure free hydrocyanic acid.

In some cases, it is also possible to isolate in limited amounts the intermediately-formed intermediate product of the formula A (A)

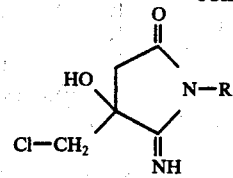

Suitable solvents for the reaction are inert solvents. It is advantageous to use solvents such as water or alcohols (methanol, ethanol, isopropanol, glycols, cellosolve, glycerin, etc.), also phenol or dioxane, as well as analogous solvents. The reaction performed in water yields, for example, solely N-phenylimide derivatives of the formula Ia, which in some cases can be converted by heating in ethanol, again in the presence of cyanide ions, into N'-phenylimino derivatives Ib. The reaction performed in alcohol yields derivatives of the formula Ib directly. Cyanide ions can be used in catalytic amounts or in larger amounts. Equimolar amounts have proved to be advantageous. By a $C_1$-$C_4$-alkyl group itself or as moiety of another substituent are meant in the formula I: methyl, ethyl, propyl, isopropyl, butyl, sec.butyl, isobutyl and tert.butyl. The term 'halogen' embraces fluorine, chlorine, bromine and iodine.

The compound chloroacetoacetanilide, the unsubstituted parent substance of the compounds of the formula II, is known, and is obtained by chlorination of diketene (e.g. in carbon tetrachloride) with the intermediate formation of chloroacetylacetic acid chloride (Cl—CH$_2$—CO—CH$_2$—COCl), and immediate further reaction with aniline [J. Am. Chem. Soc. 62, 1147 (1940)]. The other compounds of the formula II are produced in an analogous manner, whereby tertiary amines can be used as acid-binding agents. There can also be produced by the process of the invention larger groups of compounds which are not embraced by the definitions of R and R' in formula I.

The temperature values in the following production examples are given in degrees Centigrade.

EXAMPLE 1

21.2 g of 4-chloroacetoacetic acid anilide and 5.4 g of NaCN are stirred for 3 hours at 25° in 150 ml of water. The reaction mixture is filtered and the residue is washed with water and dried. There is obtained 15.5 g of 2-oxo-4-hydroxymethyl-5-imino-Δ$^3$-N-phenylpyrroline in the form of colourless crystals, m.p. 86°–88° (from ethanol).

$C_{11}H_{10}N_2O_2$; calculated: C, 65.34; H, 4.98; N, 13.85%; found: C, 65.23; H, 4.93; N, 13.86%.

Structure confirmed according to N.M.R. and X-ray spectroscopy.

EXAMPLE 2 a. 21.2 g of 4-chloroacetoacetic acid anilide and 5.4 g of NaCN are stirred for 72 hours at 0°–5° in 150 ml of ethanol. The reaction mixture is filtered and the residue is washed with a small amount of ethanol and water and then dried. There is obtained 3 g of 2-oxo-4-chloromethyl-4-hydroxy-5-imino-N-phenylpyrrolidine, an intermediate of the formula A, in the form of yellowish crystals, m.p. 180° (decomposition).

$C_{11}H_{11}ClN_2O_2$ calculated: C, 55.35. H, 4.65; Cl, 14.85, N, 11.74%; found: C, 55.44; H, 4.64; Cl, 15.13; N, 11.62%.

b. The alcoholic filtrate of the Example 2a is concentrated to a half; it is then poured into 200 ml of water and extracted with ether. After removal of the ether by distillation there is obtained 13.3 g of 2-oxo-4-hydroxymethyl-5-phenylimino-$\Delta^3$-pyrroline (crystallisable from chloroform, yellow crystals, slightly soluble in alcohol) m.p. 117°–119°.

$C_{11}H_{10}N_2O_2$ calculated: C, 65.34; H, 4.98; N, 13.85; O, 15.82%; found: C, 65.06; H, 5.04; N, 14.09; O, 15.91%.

Structure confirmed according to N.M.R. and X-ray spectroscopy.

EXAMPLE 3

28 g of 4-chloroacetoacetic acid-3', 4'-dichloroanilide, m.p. 86°–88°, and 5.4 g of NaCN are stirred for 72 hours at 0–5° in 150 ml of alcohol. The reaction mixture is filtered and the residue is washed with alcohol and water and then dried. There is obtained 16 g of 2-oxo-4-hydroxymethyl-5-[3',4'-dichlorophenylimino]-$\Delta^3$-pyrroline (crystallisable from alcohol, yellow crystals) m.p. 182°–184°.

$C_{11}H_8Cl_2N_2O_2$ calculated: C, 48.7; H, 3.0; N, 10.3; Cl, 26.1%; found: C, 48.5; H, 3.0; N, 10.4; Cl, 26.0%.

EXAMPLE 4

23 g of 4-chloroacetoacetic acid-4'-fluoroanilide, m.p. 119°–121°, and 5.4 g of NaCN are stirred for 3 hours at 25° in 150 ml of water. The suspension is filtered under suction and the residue is washed with water until neutral and dried. There is obtained 17.1 g of 2-oxo-4-hydroxy-methyl-5-imino-$\Delta^3$-N-4'-fluorophenylpyrroline in the form of colourless crystals, m.p. 167°–168° (from alcohol). Structure confirmed according to N.M.R.

If there is used, instead of the employed amount of 4-chloroacetoacetic acid-4'-fluoroanilide, 23 g of 4-chloroacetoacetic acid-2'-fluoroanilide, m.p. 103°–104°, then there is obtained 15.5 g of 2-oxo-4-hydroxy-methyl-5-imino-$\Delta^3$-N-2'-fluorophenylpyrroline, m.p. 127–128° (from chloroform).

EXAMPLE 5

34.8 g of 4-chloroacetoacetic acid-3', 5'-bistrifluoromethylanilide, m.p. 128°–129°, and 5.4 g of NaCN are stirred for 72 hours at 0–=° in 150 ml of alcohol. The reaction mixture is concentrated to a half; 200 ml of water is added and extraction is performed with ether. After removal of the ether by distillation, there is obtained 18.6 g of 2-oxo-4-hydoxy-methyl-5-[3',5'-bistrifluoromethylphenylamino]-$\Delta^3$-pyrroline (yellow crystals from chloroform); m.p. 138°–139°. Structure confirmed by N.M.R.

EXAMPLE 6

22.6 g of 4-chloroacetoacetic acid-4'-methylanilide, m.p. 145°–146°, which is obtained by chlorination of diketene and reaction of the chloroacetylacetic acid chloride with 4-methylaniline in the presence of triethylamine, is stirred with 5.4 g of NaCN for 3 hours at 25° in 150 ml of water. The suspension is filtered with suction and the residue is washed with water and dried. There is obtained 17 g of 2-oxo-4-hydroxy-methyl-5-imino-$\Delta^3$-N-4'-methylphenylpyrroline, m.p. 102°–105°, (from ethanol).

The following compounds of the formula Ib are produced in this manner or by one of the production variants given in the foregoing:

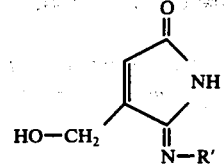

(Ib).

| Comp. No. | R' | m.p.[° C] |
|---|---|---|
| 1.1 | —$C_6H_5$ | 117–119° |
| 1.2 | —$C_6H_4Cl(4)$ | 166–168° |
| 1.3 | —$C_6H_3Cl_2(3,4)$ | 182–184° |
| 1.4 | —$C_6H_3Cl_2(3,5)$ | 167–168° |
| 1.5 | —$C_6H_4Cl(3)$ | |
| 1.6 | —$C_6H_4Br(3)$ | |
| 1.7 | —$C_6H_2Cl_3(3,4,5)$ | |
| 1.8 | ![CH3-phenyl-Cl] | |
| 1.9 | —$C_6H_3(CH_3)_2(2,4)$ | |
| 1.10 | —$C_6H_4(isoC_3H_7)$ (3) | |
| 1.11 | —$C_6H_4(isoC_3H_7)$ (4) | |
| 1.12 | —$C_6H_4$—$C_2H_5$ (4) | |
| 1.13 | —$C_6H_4$—$N(CH_3)_2$ (4) | |
| 1.14 | ![phenyl-NH-nC3H7] | |
| 1.15 | —$C_6H_4CN(4)$ | |
| 1.16 | ![phenyl-O-secC4H9] | |
| 1.17 | —$C_6H_3Br_2(3,5)$ | |
| 1.18 | —$C_6H_3Br_2(3,4)$ | |
| 1.19 | —$C_6H_4F(4)$ | 122–123° |
| 1.20 | —$C_6H_4F(3)$ | 147–148° |
| 1.21 | —$C_6H_4F(2)$ | |
| 1.22 | ![phenyl-CF3] | 138–139° |
| 1.23 | ![phenyl-CF3,Cl,CF3] | 161–162° |
| 1.24 | —$C_6H_4$—$CH_3(4)$ | |
| 1.25 | —$C_6H_4$—$OCH_3(4)$ | |
| 1.26 | —$C_6H_4$—$NO_2(3)$ | |

The following compounds of the formula Ia are produced according to the corresponding Examples or by one of the production variants given in the foregoing:

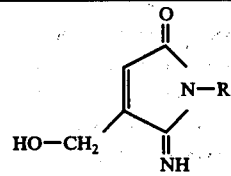

(Ia).

| Comp. No. | R | m.p. [° C] |
|---|---|---|
| 2.1 | —$C_6H_5$ | 86 – 88° |
| 2.2 | —$C_6H_4Cl(4)$ | 131 – 132° |
| 2.3 | —$C_6H_3Cl_2(3,4)$ | 146 – 148° |
| 2.4 | —$C_6H_3Cl_2(3,5)$ | 133 – 134° |
| 2.5 | —$C_6H_4Cl(3)$ | |
| 2.6 | —$C_6H_4Br(3)$ | |
| 2.7 | —$C_6H_2Cl_3(3,4,5)$ | |

-continued $$\text{(Ia)}$$

structure: 2-oxo-4-hydroxymethyl-5-imino-pyrroline with HO—CH₂ and N—R, NH substituents

| Comp. No. | R | m.p. [° C] |
|---|---|---|
| 2.8 | —C₆H₄—CH₃/Cl (structure: phenyl with CH₃ and Cl) | |
| 2.9 | —C₆H₃(CH₃)₂(2,4) | |
| 2.10 | —C₆H₄(isoC₃H₇)(3) | |
| 2.11 | —C₆H₄(isoC₃H₇)(4) | |
| 2.12 | —C₆H₄—4—2H₅(4) | |
| 2.13 | —C₆H₄—N(CH₃)₂(4) | |
| 2.14 | —C₆H₄—NH—nC₃H₇ | |
| 2.15 | —C₆H₄CN(4) | |
| 2.16 | —C₆H₄—O—secC₄H₉ | |
| 2.17 | —C₆H₃Br₂(3,5) | |
| 2.18 | —C₆H₃Br₂(3,4) | |
| 2.19 | —C₆H₄F(4) | 167 – 168° |
| 2.20 | —C₆H₄F(3) | |
| 2.21 | —C₆H₄F(2) | 127 – 128° |
| 2.22 | —C₆H₃(CF₃)₂ | |
| 2.23 | —C₆H₃(Cl)(CF₃) | |
| 2.24 | —C₆H₄—CH₃(4) | 102 – 105° |
| 2.25 | —C₆H₄—OCH₃(4) | 125 – 127° |
| 2.26 | —C₆H₄—NO₂(3) | |

Fungi occurring on plants or on parts of plants (fruit, blossom, foliage, stems, tubers or roots) can be inhibited or destroyed with these active substances, with parts of the plants subsequently growing being then also unaffected by such fungi. To be mentioned is, for example, the Cercospora infestation of peanuts, sugar beet, soya beans, etc., or the Rhizoctonia infestation of varieties of cabbage, which can be lastingly controlled with active substances of the formula I, especially since these compounds also exhibit a systemic action.

The said compounds can also be used as dressing agents for the treatment of seed (fruit, tubers, grain) and plant cuttings for protection against fungus infections such as Tilletia caries, as well as against phytopathogenic fungi present in the soil.

The novel process of the invention concerns, in particular, the production of the compounds of the formula I wherein one of the two substituents R and R' represents an unsubstituted phenyl ring, or a phenyl ring substituted by $C_1$-$C_4$-alkyl, $C_1$-$C_4$-alkoxy, $C_1$-$C_4$-hydroxyalkyl, $C_1$-$C_4$-alkylamino, ($C_1$-$C_4$-alkyl)₂amino, halogen or cyano, whilst the other of the two substituents R and R' represents hydrogen. Amongst these, those are preferred in which the phenyl ring is unsubstituted, or substituted by methyl, ethyl, isopropyl, methoxy, ethoxy, chlorine or bromine Microbicidally important individual compounds are, inter alia:
2-oxo-4-hydroxymethyl-5-imino-Δ³-N-(4-chlorophenyl)-pyrroline,
2-oxo-4-hydroxymethyl-5-[3',4'-dichlorophenylimino]-Δ³-pyrroline,
2oxo-4-hydroxymethyl-5-[3',5'-dichlorophenylimino-]-Δ³-pyrroline;
as well as, in particular, the compound
2-oxo-4-hydroxymethyl-5-imino-Δ³-N-(4-fluorophenyl)-pyrroline.

In the German 'Offenlegungsschrift' No. 1,949,435 there is mentioned the weak fungicidal action of the structurally similar compound N-phenyl-2-methylmaleinimide, which in its action is clearly inferior to the compounds of the present formula I.

The compounds of the formula I surprisingly also have a favourable plant-growth-regulating action. There may be mentioned, for example, their abscission properties, such as fruit abscission or blossom-thinning, which are especially pronounced in the case of the compound of the formula
2-oxo-4-hydroxymethyl-5-phenylimino-Δ³-pyrroline.

In order to broaden or modify their range of action, the active substances of the formula I can be mixed with prior known fungicides, bactericides, fungistatics or bacteriostatics, but also with insecticides, acaricides or herbicides; and, by virtue of their systemic action which enables an application to be made to the soil, also with nematicides, molluscicides, or rodenticides, with in some cases synergistically heightened effects being achieved.

The compounds of the formula I can be used on their own or together with suitable carriers and/or further additives. Suitable carriers and additives can be solid or liquid and they correspond to the substances common in formulation practice, such as natural or regenerated mineral substances, solvents, dispersing agents, wetting agents, adhesives, thickening agents, binding agents or fertilisers.

The content of active substance in commerical compositions is between 0.1 and 90%.

For application, the compounds of the formula I can be in the following forms (the percentage weight values in brackets represent advantageous amounts of active substance):

solid preparations: dusts and scattering agents (up to 10%), granulates [coated granulates, impregnated granulates and homogeneous granulates] (1to 80%);

liquid preparations:
a. active-substance concentrates dispersible in water: wettable powders and pastes (25–90% in the commercial packing, 0.01 to 15% in ready-for-use solution); emulsion and solution concentrates (10 to 50%; 0.01 to 15% in ready-for-use solution);
b. solutions (0.1 to 20%).

The active substances of the formula I of the present invention can be formulated, for example, as follows:

Dusts

The following substances are used to prepare (a) a 5% dust and (b) a 2% dust:
a.

5 parts of Active Substance,
95 parts of talcum;
b.
2 parts of Active Substance,
1 part of highly dispersed silicic acid,
97 parts of talcum.

The active substances are mixed and ground with the carriers, and can be applied by scattering in this form.

Granulate

The following substances are used to produce a 5% granulate:
5 parts of Active Substance,
0.25 part of epichlorohydrin,
0.25 part of cetyl polyglycol ether,
3.50 parts of polyethylene glycol,
91 parts of kaolin (particle size 0.3 - 0.8 mm).

The active substance is mixed with epichlorohydrin and the mixture is dissolved with 6 parts of acetone; the polyethylene glycol and cetyl polyglycol ether are then added. The solution thus obtained is sprayed onto kaolin, and the acetone is subsequently evaporated off in vacuo. A microgranulate of this kind is advantageously used for the control of soil fungi.

Wettable powders

The following constituents are used to produce (a) a 70%, (b) a 40%, (c) and (d) a 25% and (e) a 10% wettable powder:
a.
70 parts of Active Substance,
5 parts of sodium dibutylnaphthyl sulphonate,
3 parts of naphthalenesulphonic acid/phenolsulphonic acid/formadehyde condensate 3:2:1,
10 parts of kaolin,
12 parts of Champagne chalk;
b.
40 parts of Active Substance,
5 parts of sodium lignin sulphonate,
1 parts of sodium dibutyl-naphthalene sulphonate,
54 parts of silicic acid;
c.
25 parts of Active Substance,
4.5 parts of calcium lignin sulphonate,
1.9 parts of Champagne chalk/hydroxyethyl cellulose mixture (1:1),
1.5 parts of sodium dibutyl-naphthalene sulphonate,
19.5 parts of silicic acid,
19.5 parts of Champagne chalk, 28.1 parts of kaolin;
d.
25 parts of Active Substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin;
e.
parts of Active Substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers together with the additives, and the mixture is then ground in the appropriate mills and rollers. There are obtained wettable powders having excellent wetting and suspension properties, which powders can be diluted with water to obtain suspensions of any desired concentration, and these can be used, in particular, for leaf application.

Emulsifiable concentrates

The following substances are used to produce a 25% emulsifiable concentrate:
25 parts of Active Substance,
2.5 parts of epoxidised vegetable oil,
10 parts of an alkylarylsulphonate/fatty alcohol polyglycol ether mixture,
5 parts of dimethylformamide,
57.5 parts of xylene.

There can be produced from such concentrates, by dilution with water, emulsions of any desired concentration, which are suitable, in particular for leaf application.

BIOLOGICAL EXAMPLE

Action against *Cercospora personata* (=C.arachidicola) on peanut plants

Three-week-old peanut plants were sprayed with a spray liquor prepared from wettable powder of the active substance (0.02% of active substance). After about 12 hours, the treated plants were dusted with a conidiospore suspension of the fungus. The infested plants were then incubated for about 24 hours at >90% relative humidity, and afterwards transferred to a greenhouse at about 22° C. The fungus infestation was assessed after 12 days.

In comparison with the untreated control plants, the plants treated with active substances of the formula I exhibited as a rule only a slight fungus infestation or practically none at all.

I claim:

1. Process for the production of iminopyrrolinones of the formula I ,02/0010

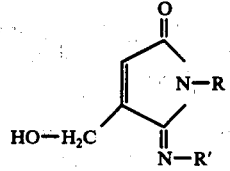

(I)

wherein one of the two substituents R and R' represents a phenyl ring unsubstituted, or substituted by $C_1$-$C_4$-alkyl, $C_1$-$C_4$-alkoxy, $C_1$-$C_4$-hydroxyalkyl, $C_1$-$C_4$-alkylamino, $(C_1$-$C_4$-alkyl$)_2$amino, halogen, nitro or cyano, whilst the other of the two substituents R and R' represents hydrogen, which process comprises reacting a chloroacetoacetanilide of the formula II

in the presence of cyanide ions, in an inert solvent in the temperature range of 0° to 80° C.

2. Process according to claim 1, wherein there are produced compounds of the formula I wherein one of the two substituents R and R' represent a phenyl ring unsubstituted, or substituted by $C_1$-$C_4$-alkyl, $C_1$-$C_4$-alkoxy, $C_1$-$C_4$-hydroxyalkyl, $C_1$-$C_4$-alkylamino, $(C_1$-$C_4$-alkyl$)_2$ amino, halogen or cyano, whilst the other of the two substituents R and R' represents hydrogen.

3. Process according to claim 2, wherein there are produced compounds of the formula I in which the phenyl ring R or R' is unsubstituted or is substituted by methyl, ethyl, isopropyl, methoxy, ethoxy, chlorine or bromine.

4. Process according to claim 1, wherein the solvent used is water or an alcohol.

5. Process according to claim 2, for the production of compounds of the formula Ia

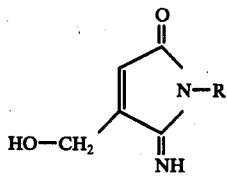
(Ia)

in which process the solvent used is water.

6. Process according to claim 2, for the production of compounds of the formula Ib (Ib)

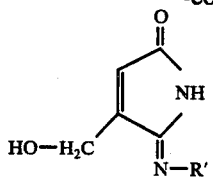

in which process the solveent used is an alcohol.

7. Process according to claim 6, wherein the alcohol is ethanol.

8. Process according to claim 5, wherein the source of the cyanide ions is an alkali cyanide.

9. Process according to claim 8, wherein sodium cyanide is used in equimolar amounts.

10. Process according to claim 5, wherein the reaction is performed at between 0° and 30° C.

11. Process according to claim 2, in which the compound produced is 2-oxo-4-hydroxymethyl-5-imino-$\Delta^3$-N-(4-fluorophenyl)-pyrroline.

12. Process according to claim 3, in which the compound produced is 2-oxo-4-hydroxymethyl-5-phenylimino-$\Delta^3$-pyrroline.

13. Process according to claim 6, wherein the source of the cyanide ions is an alkali cyanide.

14. Process according to claim 13 wherein sodium cyanide is use in equimolar amounts.

15. Process according to claim 6, wherein the reaction is performed at between 0° and 30° C.

* * * * *